US009386940B2

(12) United States Patent
Friman

(10) Patent No.: US 9,386,940 B2
(45) Date of Patent: Jul. 12, 2016

(54) MRI INVOLVING A LOCAL RF COIL BEING MOVABLE RELATIVE TO A PEDIATRIC PATIENT CARRIER

(75) Inventor: Olli Tapio Friman, Gainesville (FI)

(73) Assignee: Koninklijke Philips N.V., Eindhoven (NL)

( * ) Notice: Subject to any disclaimer, the term of this patent is extended or adjusted under 35 U.S.C. 154(b) by 119 days.

(21) Appl. No.: 14/009,350

(22) PCT Filed: Apr. 12, 2012

(86) PCT No.: PCT/IB2012/051788
§ 371 (c)(1),
(2), (4) Date: Oct. 2, 2013

(87) PCT Pub. No.: WO2012/143825
PCT Pub. Date: Oct. 26, 2012

(65) Prior Publication Data
US 2014/0031671 A1   Jan. 30, 2014

Related U.S. Application Data

(60) Provisional application No. 61/476,463, filed on Jan. 18, 2011.

(51) Int. Cl.
| A61B 5/055 | (2006.01) |
| G01R 33/30 | (2006.01) |
| G01R 33/34 | (2006.01) |
| G01R 33/3415 | (2006.01) |
| A61B 6/04 | (2006.01) |

(52) U.S. Cl.
CPC ............. *A61B 5/0555* (2013.01); *G01R 33/30* (2013.01); *G01R 33/34007* (2013.01); *A61B 6/0407* (2013.01); *A61B 2503/04* (2013.01); *G01R 33/3415* (2013.01); *G01R 33/34084* (2013.01)

(58) Field of Classification Search
CPC ............. A61B 5/0555; A61B 2503/04; G01R 33/34084; G01R 33/34007; G01R 33/34046
USPC ......................................................... 600/415
See application file for complete search history.

(56) References Cited

U.S. PATENT DOCUMENTS

| 4,727,328 A | 2/1988 | Carper |
| 5,065,760 A | 11/1991 | Krause |
| 5,307,806 A * | 5/1994 | Jones ............................ 600/422 |

(Continued)

FOREIGN PATENT DOCUMENTS

| JP | 0871053 A | 3/1996 |
| JP | 2010207464 A | 9/2010 |
| WO | 2009146522 A1 | 12/2009 |

*Primary Examiner* — Long V Le
*Assistant Examiner* — Bradley Impink

(57) ABSTRACT

A pediatric patient handling assembly includes a carrier on which a pediatric patient is positioned and prepared for magnetic resonance imaging (MRI). The carrier carrying the pediatric patient is set on a support table of an MRI scanner. The support table includes a local RF coil assembly mounted on the support table. The carrier is slid along the support table and into engagement with the local RF coil assembly. Interacting guide surfaces on the carrier and the local RF coil assembly align and engage the carrier along a longitudinal axis of the support table. The local RF coil assembly includes a pivotally mounted anterior coil which is lowered towards a base of the support table into an imaging or operating position. The support table, with the engaged local RF coil assembly, carrier and pediatric patient, is translated into a magnetic imaging region of the MRI scanner.

18 Claims, 6 Drawing Sheets

(56) References Cited

U.S. PATENT DOCUMENTS

| | | | |
|---|---|---|---|
| 2002/0173717 A1* | 11/2002 | Rohling | A61B 5/0555 600/415 |
| 2004/0015074 A1* | 1/2004 | Srinivasan | G01R 33/34046 600/422 |
| 2004/0075437 A1* | 4/2004 | Srinivasan | G01R 33/34046 324/318 |
| 2005/0045650 A1* | 3/2005 | Tippman | 220/828 |
| 2005/0107686 A1* | 5/2005 | Chan et al. | 600/422 |
| 2005/0113668 A1* | 5/2005 | Srinivasan | A61B 5/416 600/411 |
| 2008/0214925 A1 | 9/2008 | Wilson | |
| 2010/0102604 A1* | 4/2010 | Barnes et al. | 297/250.1 |
| 2012/0126814 A1* | 5/2012 | Fischer | G01R 33/30 324/318 |

* cited by examiner

MRI INVOLVING A LOCAL RF COIL BEING MOVABLE RELATIVE TO A PEDIATRIC PATIENT CARRIER

CROSS-REFERENCE TO PRIOR APPLICATIONS

This application is the U.S. National Phase application under 35 U.S.C. §371 of International Application No. PCT/IB2012/051788, filed on Apr. 12, 2012, which claims the benefit of U.S. Provisional Patent Application No. 61/476,463, filed on Apr. 18, 2011. These applications are hereby incorporated by reference herein.

The present application relates to a device and system for handling a patient within a magnetic resonance imaging (MRI) assembly. It finds particular application in conjunction with a device and system for handling a pediatric patient within an MRI system configured for use by an adult patient. However, it is to be understood that it also finds application in other diagnostic imaging and patient handling scenarios, and is not necessarily limited to the aforementioned application.

MRI scanners scan a patient to provide detailed images of afflicted areas to aid healthcare providers in their diagnosis of ailments that may be present in the patient. MRI scanners utilize powerful magnetic fields to align protons within the body of a patient. Radio frequency (RF) fields are applied to alter the alignment of this magnetization which causes the protons to resonate to produce a weak RF field that is detected, recorded and transformed into detailed images of the scanned area. A large magnetic coil produces the main magnetic field and magnetic field gradient coils apply gradient magnetic fields for spatially encoding the resonance RF signal. Additionally, the patient is positioned at a predetermined location within an imaging region of the magnetic coil to allow the MRI scanner to produce quality images of the patient.

MRI scanners are typically mounted in RF shielded rooms. When local coils are used to receive the resonance signals, patients are aligned and fitted to the local RF coil prior to being inserted into the imaging region of the MRI scanner. RF coils that are too large and cumbersome to attach directly on the patient and are often rigidly attached to a patient table that supports the patient and translates the patient into and out of the imaging region. Generally, the patent is fitted to the RF coil on the patient table or elsewhere within the shielded room which prevents the MRI scanner from being used to image other patients during set up. Due to the expense of MRI scanners, medical institutions typically purchase scanners that are sized to accept normal adult patients. Smaller scale scanners, sized specifically for smaller sizes of patients, are typically not available in most medical institutions.

Moreover, pediatric patients, particularly neonatal patients who need imaging typically are in neonatal intensive care wards and travel with an array of monitors and medical accessories. These monitors and accessories as well as the patient supports and restraints for positioning a pediatric patient during imaging increase the duration of the patient preparation time. Because this preparation is typically performed on the patient support, the time between patient imaging procedures is increased and patient throughput is decreased. Moreover, the increased preparation time increases the duration that the neonatal patient is absent from highest levels of care.

Therefore, there remains a need to provide a streamlined process for patient preparation. Additionally, there is a need for enabling patient positioning and fitting to a RF coil outside of the shield room that reduces patient preparation time. Further, there is a need for positioning a pediatric patient to an RF coil and a within an imaging region of an MRI assembly that is configured for a normal adult patient accurately and quickly.

The present application provides a new and improved device and method which overcome the above-referenced problems and others.

In accordance with one aspect, a pediatric patient handling assembly includes a local RF coil assembly defining a pediatric patient receiving region and configured to be mounted to a patient support table of a magnetic resonance imaging scanner. A pediatric patient carrier is configured to receive the pediatric patient and slide longitudinally into engagement with the local RF coil assembly with at least a portion of the pediatric patient disposed in the pediatric patient receiving region.

In accordance with a more limited aspect, the patient carrier includes a base surface which supports the associated pediatric patient and configured to slidingly translate longitudinally to interact with the local RF coil disposed on the table. Carrier shoulders are attached to a first end of the base surface and are configured to engage a portion of the RF coil. A head region is aligned adjacent to the carrier shoulders at the first end to support a head of the associated pediatric patient.

In accordance with another aspect, a method for handling the pediatric patient within an MRI scanner configured to accept and evaluate an adult patient. The method includes mounting the local RF coil assembly to a patient support table. The pediatric patient is arranged within a carrier. The carrier is positioned on the patient support table. The patient carrier is moved into engagement with the local RF coil assembly. The table with the engaged carrier and RF coil assembly are moved into an imaging region of an MRI scanner and the patient is scanned within the MRI scanner.

One advantage resides in reducing the patient preparation time in the shielded room.

Another advantage resides in facilitating imaging a pediatric, particularly neonatal, patient in an MRI scanner that has been configured for a full size adult patient.

Yet another advantage resides in positioning a patient accurately within the RF coil and adds flexibility to patient handling.

Yet a further advantage resides in facilitating handling of cables or tubes extending from the patient to associated medical instrumentation. The handling of the patient and associated instrumentation is simplified.

Still yet another advantage resides in ready removal and release of the patient in an emergency.

A further advantage resides in a carrier device that is stackable with a plurality of like carriers for ease in storage or bulk transport.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
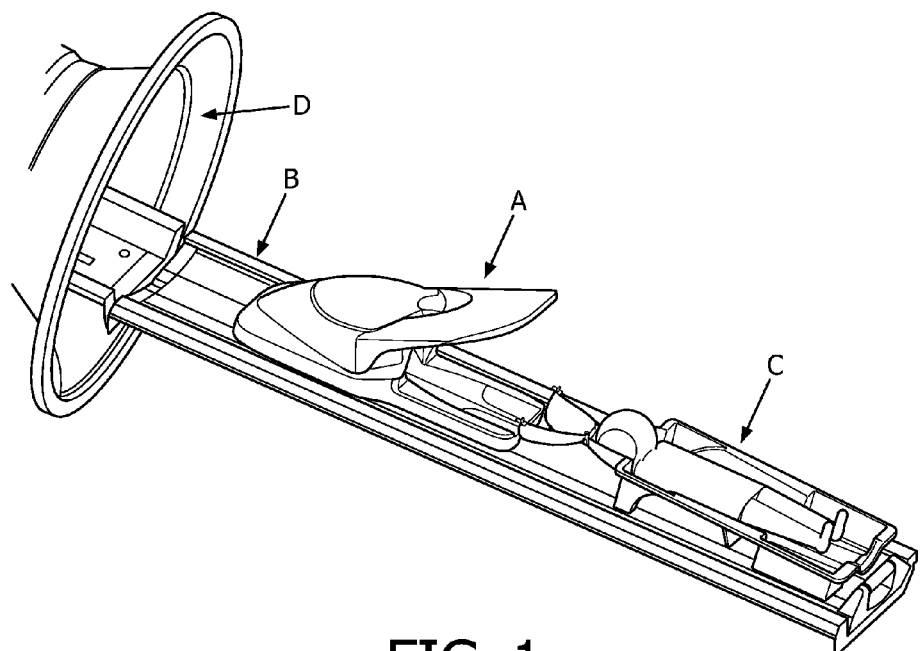
FIG. 1 is a perspective view of a carrier device on a patient table with an associated patient ready to engage a local RF coil assembly on the patient table.

With reference to FIG. 1, a pediatric local RF coil assembly A is mounted to a patient supporting table or couch B which translates to move a patient into and out of an imaging region D of a diagnostic scanner, particularly an MRI scanner. A pediatric patient is positioned in a pediatric patient carrier C along with any monitors and medical apparatus in preparation for imaging. The preparation can be done outside of an MRI shielded room. The carrier C with the pediatric patient is carried into the shielded room, placed on the patient support table B, and slid longitudinally into engagement with the local RF coil assembly A. After the RF coil assembly A is closed, the patient support table B along with the local RF coil assembly, the patient carrier, and the patient are transported into the imaging region D of the MRI scanner. After imaging, this process is reversed.

Figure 2:
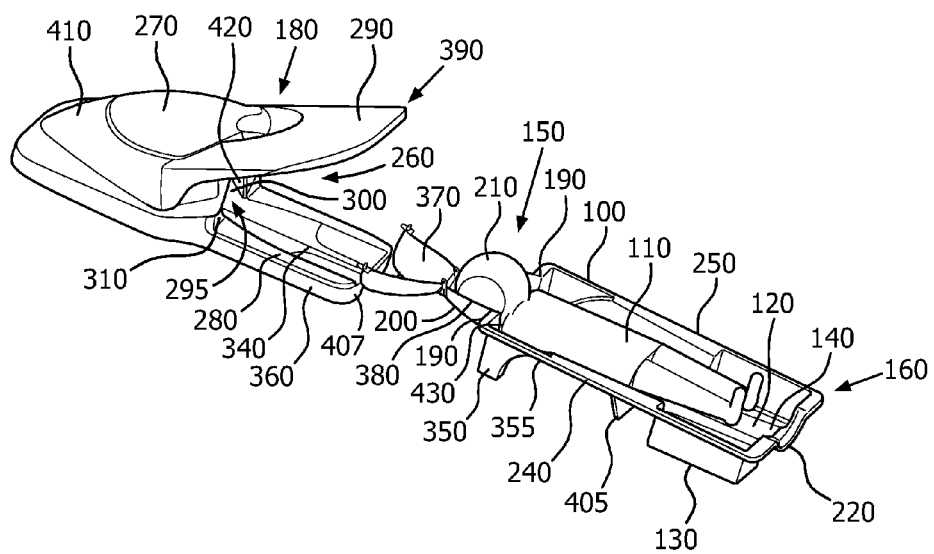
FIG. 2 is a perspective view of the carrier with the associated patient engaged ready to be received in the local RF coil assembly.

With reference to FIG. 2, a movable, portable pediatric patient carrier A, 100 is configured to hold an associated pediatric patient 110 in alignment with its longitudinal axis. The patient carrier C, 100 has a bassinet like configuration including a base 120 with a first side 130 opposite a second side 140 and a first end 150 opposite a second end 160. The base 120 is configured to be slidably supported on an associated patient support table or couch D, 170 (See FIG. 1). The carrier 100 slidingly translates along its longitudinal axis to interact with a local RF coil assembly A, 180 disposed on the table 170. The second side 140 of the base surface is configured to receive the associated pediatric patient 110.

Carrier shoulders 190 at the first end 150 are configured to engage the patient's shoulders to position the patient longitudinally in the carrier 100. The carrier shoulders 190 engage the local RF coil 180 to position the carrier 100 and, hence, the patient longitudinally relative to the local RF coil 180. A head region or cavity 200 is provided along a common plane with the base surface 120 and aligned to the carrier shoulders 190 at the first end 150 to support a head 210 of the associated pediatric patient 110. The head region 200 is positioned adjacent a central portion of the carrier shoulders 190 such that a gap extends between the carrier shoulders 190. The gap conforms to and accepts a neck of the associated pediatric patient 110 and the carrier shoulders 190 conform to each shoulder of the associated pediatric patient 110.

A grip surface 220 extends from the second end 160 of the base 120 and is configured to allow for the controlled movement of the apparatus by an associated operator (not shown). In one embodiment, the grip surface 220 is an integral flange extending from the second end 160 that conforms to a grip of the operator. However, the grip surface 220 may also comprise a handle, continuous bar, or resilient member to assist in the sliding axial translation of the movable support apparatus 100. Additionally, a second grip surface 230 extends from the first end 150 at the carrier shoulders 190 to allow multiple operators to securely handle the carrier 100 during the transport of the carrier 100 and associated patient 110. In another embodiment, grip surfaces (not shown) may be provided about the exterior of the movable support apparatus along a first longitudinal edge 240 extending lengthwise along the base surface 120 and a second longitudinal edge 250 oppositely disposed from the first longitudinal edge 240.

In one embodiment, the local RF coil 180 defines a patient receiving region 260 which accepts the first end 150 of the carrier 100. The local RF coil 180 is defined by a head coil 270, a posterior coil 280 and an anterior body coil 290. The carrier 100 is slidably translatable along the common axis with the RF coil 180 to interact with the posterior coil 280 and abuttingly engage a mating structure 295 within the region 260 of the RF coil 180. (See FIG. 3) The carrier shoulders 190 are configured to interact with the mating structure 295 of the RF coil assembly 180. In one embodiment, the mating structure 295 is located within the patient receiving region 260 and includes an inner surface 300 and a complimentary surface 310 located on a portion of the head coil 270. In one embodiment, the carrier shoulders 190 are configured to abut the complimentary surface 310 and the head region 200 of the carrier 100 is configured to extend beyond the complimentary surface 310 and engages the inner surface 300. The inner surface 300 is configured to receive the head region 200 and snuggly position the patient 110 within the region 260 at a suitable imaging position. The suitable position is a predetermined orientation of the patient 110 relative to the RF coil 180 and a magnetic imaging region D, 330 of the MRI assembly to allow for optimal magnetic imaging.

The first side 130 of the base 120 is configured to interact and align with a profile 340 or guide surface of a posterior coil 280 to allow for slidingly positioning the carrier 100 in accurate axial alignment in the imaging position within the region 260 of the RF coil 180. In one embodiment illustrated in FIGS. 1-3, the first side 130 includes at least one leg 350 that protrudes from the first side 130 and slidingly engages the table 170 and a side of the posterior coil 280. The legs 350 and interacting guide surface 355 conform to the profile 340 of the posterior coil 280 such that the head region 200 and carrier shoulders 190 at the first end 150 slide longitudinally over the posterior coil 280 as the first side 130 of the base surface 120 engages the RF coil 180. The legs 350 advance longitudinally along a side portion 360 of the posterior coil 280 while supporting the carrier 100 and maintaining contact with the table 170. The interacting guide surfaces 355 slidably engage the posterior coil profile 340 or guide surface to align the local RF coil 180 and the patient carrier 100.

In one embodiment, a transparent shield 370 is hingedly attached at the first end 150 and is conformed to the head region 200 to open and enclose the head cavity. The shield 370 is pivotably mounted to the head region 200 and can be toggled between an open position and a closed position. In the closed position, the shield 370 at least partially abuts an upturned edge 380 of the head region 200 and attaches adjacent a portion of the carrier shoulders 190. The shield 370 provides protection to the head 210 of the patient 110 from contacting the inner surface 300 of the region 260 when the carrier 100 is slidingly translated into the local RF coil 180.

The shield 370 is made of a generally clear or transparent material such as plastic or glass.

The carrier 100 is shaped to stack with a plurality of like carriers for ease in storage and bulk transport. The base 120, the carrier shoulders 190, and the head region 200 of a first carrier 100 abuttingly align with the base surface 120, the carrier shoulders 190, and the head region 200 of a second carrier 100 in a stackable arrangement. When a carrier 100 is stacked with at least one other carrier, the shield 370 is in the open position to allow one head region 200 to abuttingly align with the other head region 200. Additionally, it is preferred that the grip surfaces 220, 230, the first longitudinal edge 230, the second longitudinal edges 240, the legs 350, the guide surfaces 355, and the side portions 360 of each carrier 100 are tapered and align in a similar stackable arrangement.

Figure 3:
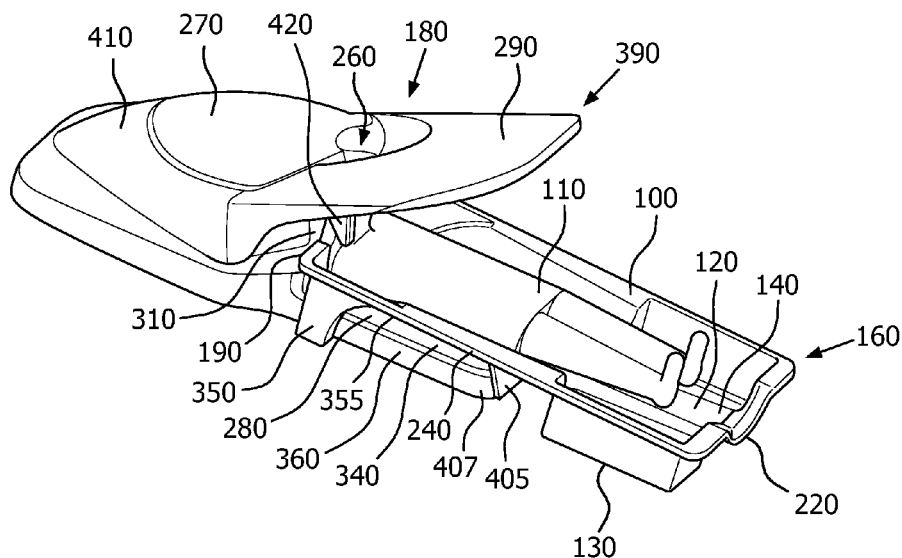
FIG. 3 is a perspective view of the carrier with the associated patient received in the local RF coil.
Figure 4:
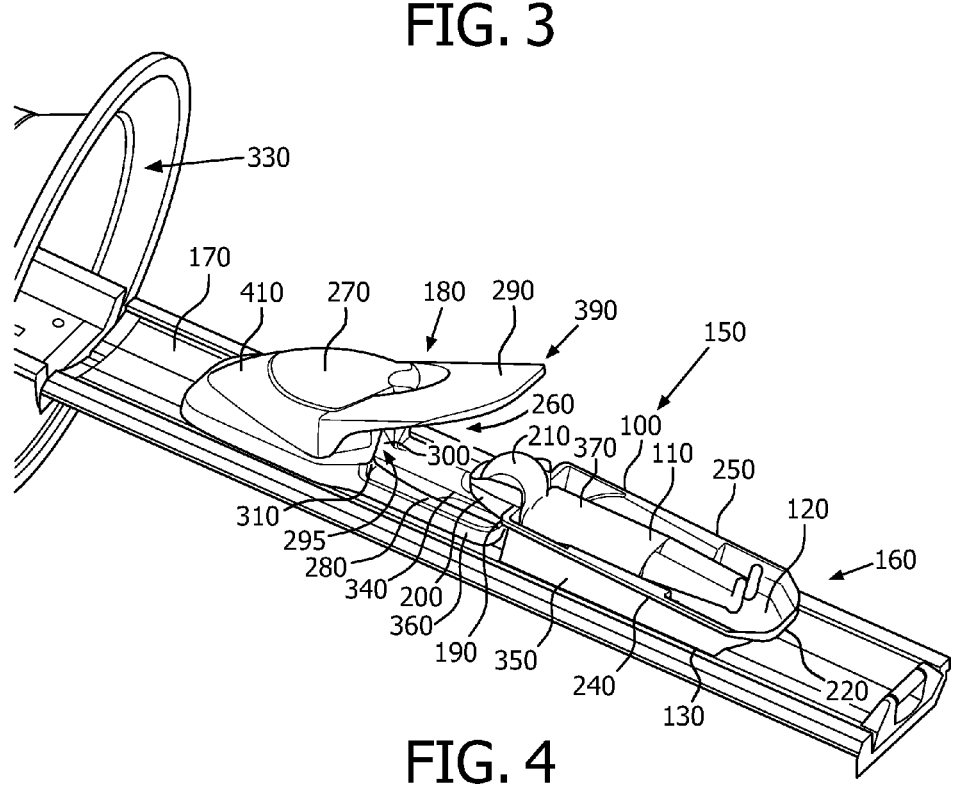
FIG. 4 is a perspective view of a second embodiment of the carrier with the associated patient and the local RF coil on the patient table of the MRI scanner.
Figure 7:
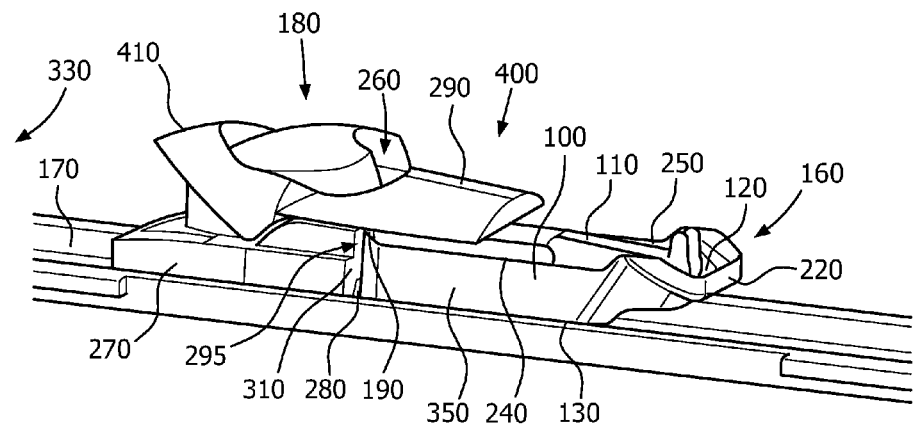
FIG. 7 is a perspective view of the second embodiment of the carrier with the associated patient received in the local RF coil with the anterior coil fully lowered on the patient table of the MRI scanner.
Figure 8:
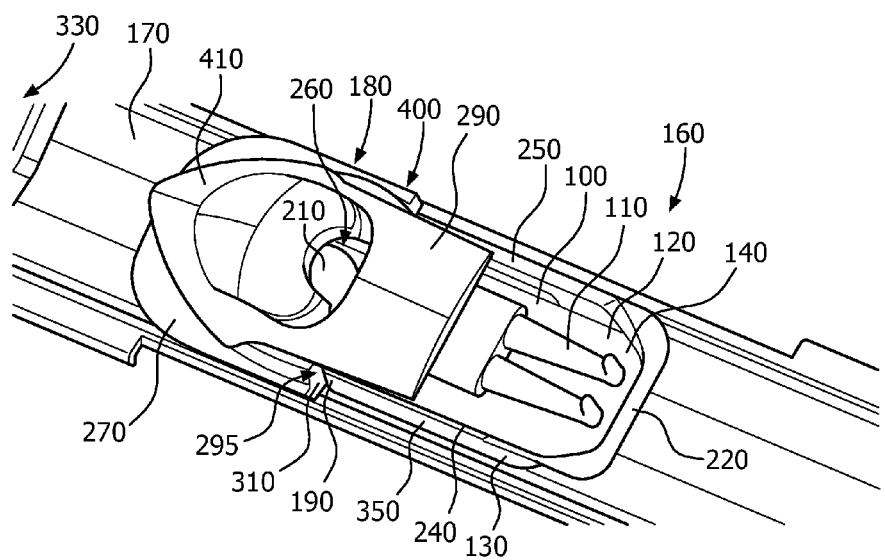
FIG. 8 is a top perspective view of the second embodiment of the carrier with the associated patient received in the local RF coil with the anterior coil lowered on the patient table of the MRI scanner.

With reference to FIG. 3, the region 260 is defined by the head coil 270, the posterior coil 280 and the anterior body coil 290. The RF coil 180 receives at least a portion of the carrier 100 within the region 260. The carrier 100 slidingly translates along the common axis on the table 170 to the suitable position 320 within the RF coil 180 in which the carrier shoulders 190 engage the complimentary surface 310 and the head region 200 engages the inner surface 300 within the region 260 of the RF coil 180. The anterior body coil 290 pivots from a resting position 390 to an operating or imaging position 400 (FIGS. 7, 8) when the carrier 100 is in the suitable position 320 if the patient requires the body to be magnetically scanned.

Figure 5:
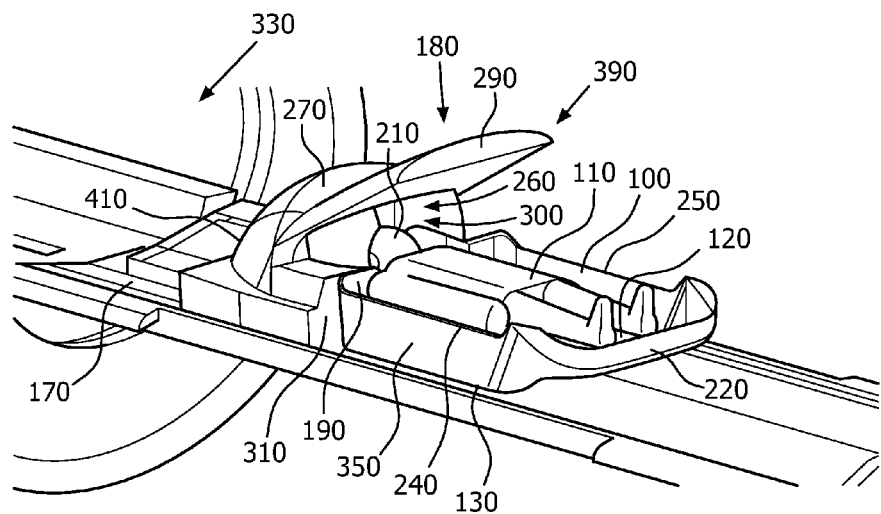
FIG. 5 is a perspective view of the second embodiment of the carrier with the associated patient received in the local RF coil on the patient table of the MRI scanner.

In one embodiment, at least a portion of the carrier 100 is positioned within the region 260 by a detent and recess or well or other suitable interlocking structure (not shown). The interlocking structure is configured to provide positive tactile feedback when the carrier 100 is properly located in the imaging position within the region 260. The feedback indication is generally a 'click' or 'snap' audible sound that signifies reception of the detent within the recess. The interlocking structure holds the carrier 100 in the imaging position without positively locking the carrier 100 therein. Additionally, the interlocking structure interacts with a release (not shown) which releases the anterior body coil 290 to rise by its biasing forces from the operating position 400 to the open position (FIG. 5) in response to the carrier 100 being withdrawn from the patient receiving region 260.

In one embodiment, the interlocking structure includes at least one ratchet member 305 extending from the anterior body coil 290 having a plurality of teeth to engage a portion of the shoulders 190 on the carrier 100. The ratchet member 305 is configured to hold the anterior body coil 290 in the operating position 400 when the carrier is at least partially positioned in the receiving region 260.

In one embodiment, the carrier 100 is aligned with the posterior coil 280 such that an abutment member 405 (see FIG. 3) extends from the first side 130 of the base surface 120. Here, the mating structure 295 includes a base edge 407 located on the posterior coil 280 that is configured to receive or abut the abutment member 405. The abutment member 405 is configured to interact with the posterior coil 280 and engages the base edge 407 when the carrier 100 is properly located in the suitable position 320 within the region 260. The abutment member 405 is optionally provided as an integral portion of the carrier 100 or is separately attached therein.

Figure 6:
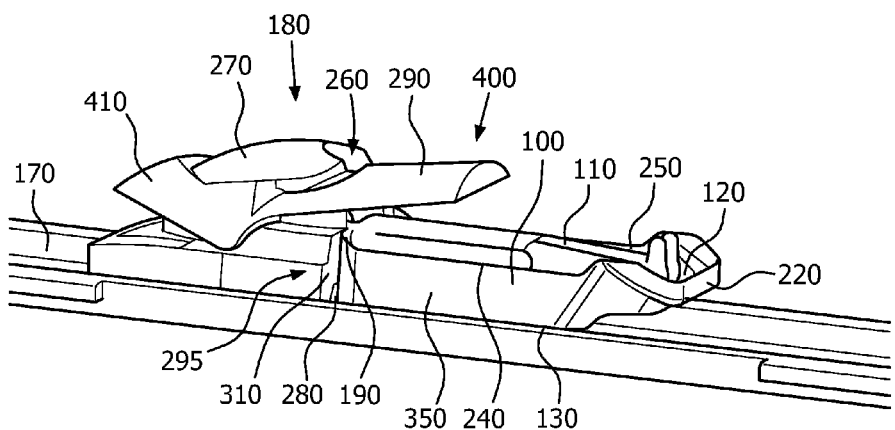
FIG. 6 is a perspective view of the second embodiment of the carrier with the associated patient received in the local RF coil with an anterior coil partially lowered on the patient table of the MRI scanner.

Once the carrier 100 is located in the region 260, the anterior body coil 290 can be manually lowered in the operating position 400. The operating position 400 of the anterior body coil 290 includes a range of positions from fully closed (FIG. 7) to partially closed (FIG. 6). Notably, the table 170 translates from a position outside of the magnetic imaging region 330 to a position within the magnetic imaging region 330 to scan the patient and produce an image. The RF coil 180 is sized to fit within the magnetic imaging region 330 when the anterior body coil 290 is in either the resting position 390 or the operating position 400.

The anterior body coil 290 is configured with a counterweight 410 to bias the anterior body coil 290 to pivot to the resting 390 or open position. In one embodiment, a cammed surface 420 engages the patient carrier 100 when the anterior body coil 290 is lowered. The cammed surface 420 is received in and engages a hollow interior of the leg 350 adjacent the shoulders 190 of the carrier 100. The anterior body coil 290 is pivoted to the resting position 390 after the carrier 100 is removed from engagement with the local RF coil 180. In an emergency during imaging, a clinician can pull the carrier 100 longitudinally away from the imaging position within the region 260 of the RF coil 180. The carrier shoulders 190 engage a sloping surface of the pawl 420 pushing the anterior body coil 290 open such that the patient 110 avoids impacting the anterior body coil 290 as the patient and carrier are sled along the patient table.

In one embodiment, the carrier 100 is independently adapted to the MRI scanner and can be configured to provide a tension safety connection for various tubes, cords, wires, or lines extending from the patient to associated instrumentation located outside the magnetic imaging region. On occasion, neonatal pediatric patients 110 are to remain attached to associated medical instrumentation such as blood pressure devices, feeding tubes, oxygen masks, intravenous bags and the like. In this situation, the tubes extend from the patient 110 to medical instrumentation while the patient is positioned within the magnetic imaging region 350. The tubes are attached to the carrier 100 with a strain relief correction to prevent an abrupt or unintended tension force being applied to the tubes in which the patient is injured or the tubes are disconnected. The tubes may be attached anywhere along the carrier 100 provided there remains a slacked connection between the patient 110 and the carrier 100 that does not impede the communication between the instrumentation and the patient 110.

Figure 10:
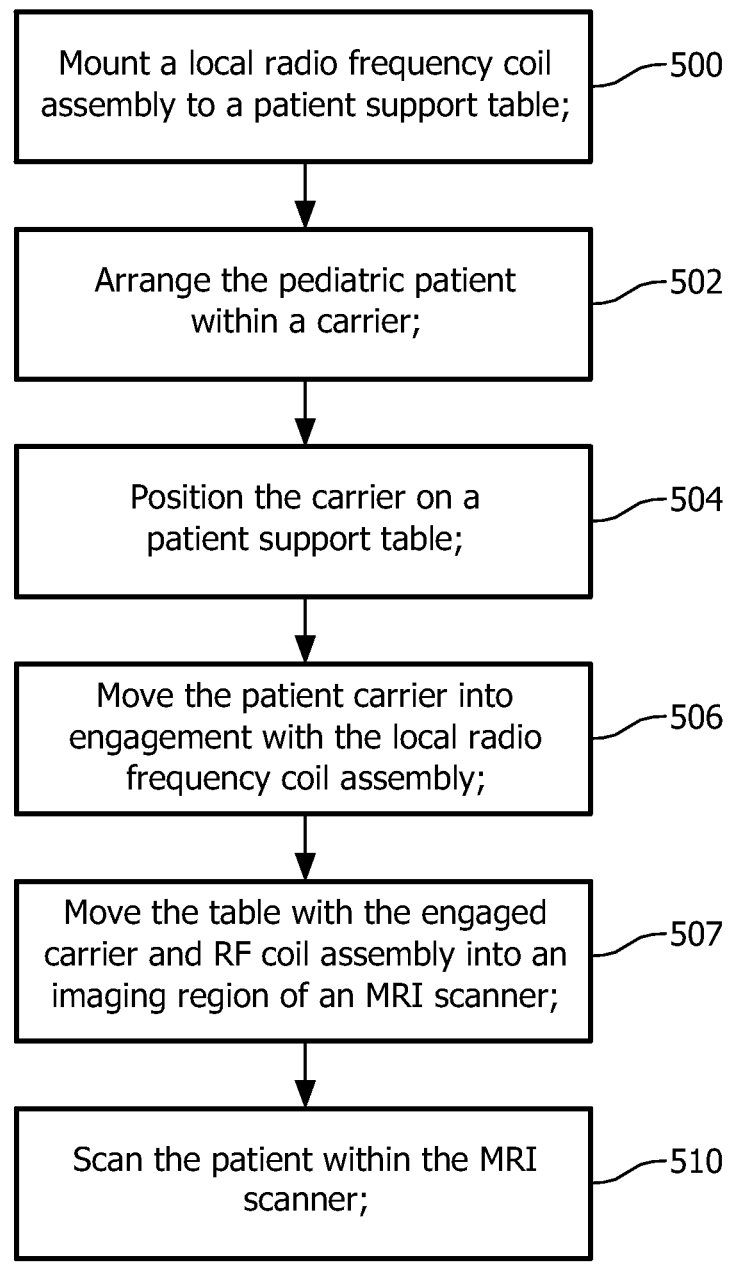
FIG. 10 is a schematic flowchart of a method for handling the pediatric patient within the MRI scanner configured to accept and evaluate an adult patient.

With reference to FIG. 10, a method of handling the pediatric patient 110 within the MRI assembly includes mounting 500 the local RF coil assembly 180 to the patient support table 170. The RF anterior body coil 280 is hingedly connected to the head coil 270 and the posterior coil 280. The RF coil defines a patient receiving region 260 to accept the carrier 100 and pediatric patient 110 for scanning. At 502, the patient, particularly a neonatal patient generally aged between 0 and 18 months old, is arranged within the carrier 100. The clinicians prepare the pediatric patient in an associated room outside of the magnetically shielded room that contains the MRI scanner.

The associated clinician then grasps the grip surface 220 or second grip surface 230 and transfers the carrier 100 and patient 110 from the associated room into the room that contains the MRI scanner. The carrier 100 along with the prepared pediatric patient 110 is positioned on the patient support table at 504.

The carrier 100 along with the patient 110 is axially aligned with the RF coil assembly 180 on the patient support table 170. The carrier 100 is moved into engagement with the local RF coil assembly 180 at 506. The interacting guide surfaces 355 and legs 350 of the carrier 100 interact with the guide surface 340 and side portion 360 of the posterior coil 280 ensuring the carrier is properly aligned within the patient receiving region 260 in the suitable position 320. The carrier shoulders 190 and head region 200 on the first end 150 of the carrier 100 are positioned within the patient receiving region 260 of the RF coil assembly 180. The carrier shoulders 190 abuttingly engage the complimentary surface 310 when the carrier is in the suitable position 320 for scanning within the RF coil 180. In another embodiment, the abutment member 405 extending from the second side 130 of the base surface 120 engages the posterior coil 280 when the carrier 100 is properly positioned in a suitable position 320 in the patient receiving region 260.

After the carrier 100 is positioned on the patient support table 170 and moved into engagement with the RF coil assembly 180, the anterior body coil 290 of the RF coil assembly is biased to the operating position 400. The anterior body coil 290 is manually moved to cover a portion of the pediatric patient 110 to be scanned. An interlock is engaged by the carrier 100 when positioned in the suitable position 320 which retains the anterior body coil 290 in the operating position 400. In one embodiment, the carrier shoulders 190 abuttingly engage the ratchet member 305 to interlock the anterior body coil 290 in the operating position 400 when the carrier is in the suitable position 320 for scanning within the RF coil 180.

At 508, the table 170 along with the engaged carrier 100 and RF coil assembly 180 is moved into the magnetic imaging region 330 of an MRI scanner. The MRI scanner is then operated to scan the patient within the imaging region 330 to produces an image at 510.

If the patient has a medical emergency and needs to be removed for immediate medical attention, the carrier 100 is manually pulled away from the local RF coil assembly 180. The anterior body coil is released from the operating position and biases open to the resting position 390. The anterior body coil 290 includes counter-weight 410 that is balanced to maintain the anterior body coil 290 in the resting position 390 (see FIG. 1) unless a counter force is introduced to pivot the anterior body coil 290 to the operating position 400. The anterior body coil 290 is maintained in the operating position 400 when the interlock is engaged by the carrier 100 positioned in the suitable position 320.

In one embodiment of the method, prior to moving the patient carrier 100 into engagement with the local RF coil assembly 180, a communication member such as tubes, conduits, cords, wires, or lines are coupled to the patient and extend from associated medical instrumentation are operatively attached to the carrier. This safety connection enables pediatric patients to remain attached to associated medical instrumentation such as blood pressure devices, feeding tubes, oxygen masks, intravenous bags when the patient is positioned within the magnetic imaging region 350. The tubes are attached to the carrier to prevent an abrupt or unintended tension force being applied to the tubes in which the patient is injured or the tubes are disconnected. The tubes may be attached anywhere along the carrier 100 provided there remains a slacked connection between the patient and the apparatus that does not impede the communication between the instrumentation and the patient.

Figure 9:
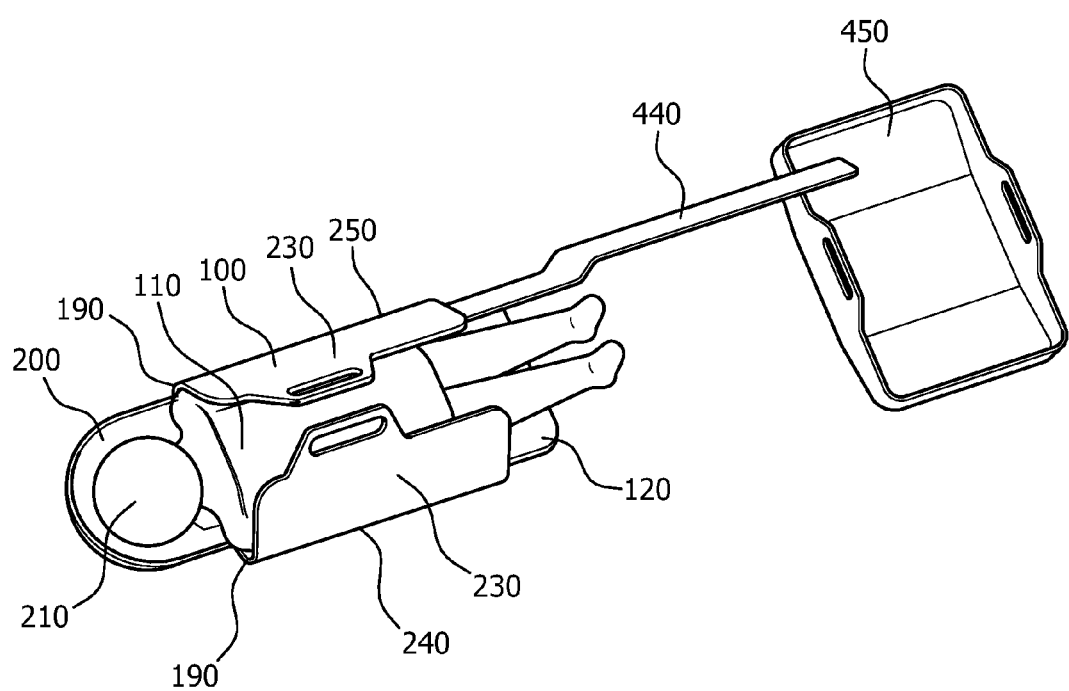
FIG. 9 is a top perspective view of the third embodiment of the carrier with the associated patient and an associated instrument carrier.

In one embodiment of the carrier 100, as illustrated in FIG. 9, the carrier 100 is attached to a cable guide 440 that extends from an instrument carrier 450. The first longitudinal edge 240 and second longitudinal edge 250 are positioned about the body of the patient. The cable guide is attached to the patient carrier 100 and the instrumentation carrier 450. The instrumentation carrier 450 is configured to be slidably positioned on the patient table 170 adjacent to the second end 160 of the carrier 100 and opposite the local RF coil assembly 180. The cable guide 440 is generally flexible and includes a predetermined length that allows movement of the instrument carrier during patient handling and transportation. The cable guide 440 acts as a tension or strain relief for tubes, conduits or wires and the like that are attached to the patient 110 and extend to associated instrumentation located on the instrumentation carrier 450. The second grip surfaces 230 are provided on the first and second longitudinal edges 240, 250 to allow an associated clinician to easily grip and transport the patient carrier 100.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A pediatric patient handling assembly comprising:
   a local radio frequency coil assembly, the radio frequency coil comprising a pediatric patient receiving region and configured to be mounted to a patient support table of a magnetic resonance imaging scanner; and
   a pediatric patient carrier configured to receive the pediatric patient, the pediatric carrier being configured to releasably engage with the local radio frequency coil assembly;
   wherein the pediatric patient carrier is configured to slidingly translate longitudinally on the patient support table into releasable engagement with the local radio frequency coil assembly.

2. The pediatric patient handling assembly according to claim 1, wherein the pediatric patient carrier comprises:
   a base arranged to support a pediatric patient and configured to slidingly translate on the patient support table longitudinally to the releasable engagement with the local radio frequency coil assembly;
   carrier shoulders adjacent to a first end of the base and configured to engage a portion of the local radio frequency coil assembly; and
   a head region adjacent to the carrier shoulders at the first end and configured to support a head of the received pediatric patient.

3. The pediatric patient handling assembly according to claim 2, wherein the pediatric patient carrier further includes:
   a grip surface extending from a second end opposite the first end, the grip surface configured to allow for a controlled movement of the pediatric carrier by an operator releasing the engagement of the pediatric carrier from the local radio frequency coil assembly.

4. The pediatric patient handling assembly according to claim 2, including:
   a shield connected to the head region of the pediatric patient carrier, the shield being configured to move into a position which is configured to move into a position to protect the head of the received pediatric patient from contacting structures adjacent the pediatric patient receiving region.

5. The pediatric patient handling assembly according to claim 1, wherein the local radio frequency coil assembly further comprises a head coil, a posterior coil, and an anterior body coil.

6. The pediatric patient handling assembly according to claim 5, wherein the posterior coil defines a guide surface and the pediatric patient carrier defines interacting guide surfaces which slidably engage the guide surface of the posterior coil to align the local radio frequency coil assembly and the pediatric patient carrier.

7. The pediatric patient handling assembly according to claim 1, wherein the pediatric carrier comprises carrier shoulders configured to abut a mating structure of the local radio frequency coil assembly when the pediatric patient carrier is received in the pediatric patient receiving region.

8. The pediatric patient handling assembly according to claim 1, wherein the pediatric patient carrier and the local radio frequency coil assembly comprise an interlocking structure which releasably holds an anterior body coil in an operating position as the pediatric patient carrier is at least partially received in the pediatric patient receiving region.

9. The pediatric patient handling assembly according to claim 8, wherein the interlocking structures comprise a detent and recess configuration that is configured to provide a tactile feedback when the pediatric patient carrier is releasably engaged with the local radio frequency coil assembly without locking the carrier in the pediatric patient receiving region.

10. The pediatric patient handling assembly according to claim 1, further comprising:
a ratchet member configured to engage the pediatric patient carrier to hold an anterior body coil in an operating position and configured to release the anterior body coil from the operating position in response to the pediatric patient carrier being withdrawn from the pediatric patient receiving region.

11. The pediatric patient handling assembly according to claim 5, wherein the anterior body coil is pivotably mounted to the local radio frequency coil assembly to pivot between a resting position and an operating position.

12. The pediatric patient handling assembly according to claim 5, wherein the anterior body coil includes a counterweight which biases the anterior body coil to pivot to a resting position.

13. A method of handling a pediatric patient within a magnetic resonance imaging scanner configured to accept and evaluate an adult patient, the method comprising acts of:
mounting a local radio frequency coil assembly to a patient support table of the magnetic resonance imaging scanner;
arranging the pediatric patient within a patient carrier;
positioning the patient carrier on the patient support table of the magnetic resonance imaging scanner;
moving the patient carrier into engagement with the local radio frequency coil assembly;
moving the patient support table of the magnetic resonance imaging scanner with the engaged carrier and the local radio frequency coil assembly into an imaging region of the magnetic resonance imaging scanner; and
scanning the pediatric patient within the magnetic resonance imaging scanner.

14. The method according to claim 13, wherein the pediatric patient is between 0 and 18 months of age.

15. The method according to claim 13, further comprising:
lowering an anterior body coil of the local radio frequency coil assembly to an operating position, in response to moving the patient carrier into the engagement with the local radiofrequency coil assembly.

16. The method according to claim 15, further comprising:
pulling the patient carrier away from the local radio frequency coil assembly, wherein the pulling releases the anterior body coil to move from the operating position to an open position.

17. The method according to claim 13, wherein the pediatric patient is arranged within the patient carrier outside of a magnetic resonance imaging shield room.

18. The method according to claim 13, further comprising an act of coupling at least one of a tube, a wire, or a conduit member to the patient, the one of the tube, the wire, or the conduit member extending from an associated medical instrumentation, and wherein the act of coupling is performed prior to the act of moving the patient carrier into the engagement with the local radiofrequency coil assembly.

\* \* \* \* \*